United States Patent [19]

Randol

[11] 3,943,267

[45] Mar. 9, 1976

[54] METHOD OF REMINERALIZING AND IMMUNIZING TOOTH ENAMEL FOR THE PREVENTION AND CONTROL OF TOOTH DECAY AND DENTAL CARIES

[75] Inventor: Neil J. Randol, Rancho Santa Fe, Calif.

[73] Assignee: Neil J. Randol, Rancho Santa Fe, Calif.

[22] Filed: Jan. 14, 1975

[21] Appl. No.: 540,860

Related U.S. Application Data

[63] Continuation-in-part of Ser. No. 471,003, May 17, 1974, abandoned.

[52] U.S. Cl. .......................... 427/2; 32/8; 424/49; 427/309; 427/343
[51] Int. Cl.² .......................................... A61K 5/02
[58] Field of Search ............. 427/2, 309, 343; 32/8; 424/49

[56] References Cited
UNITED STATES PATENTS

| | | | |
|---|---|---|---|
| 3,562,911 | 2/1971 | Walter et al. | 32/8 |
| 3,766,650 | 10/1973 | Gnecco | 32/8 |

*Primary Examiner*—Harry J. Gwinnell
*Assistant Examiner*—Dennis C. Konopacki
*Attorney, Agent, or Firm*—Harris, Kern, Wallen & Tinsley

[57] ABSTRACT

Tooth enamel is treated with a dental etching acid to leach out the positvely charged calcium ions therefrom and to provide a roughened, porous, sponge-like appearing surface which is negatively charged. Said surface is treated with the positively charged ions of the heavy metals which are ionically attracted to said negatively charged surface and deposited into and on said surface which is remineralized with said heavy metal ions to form a relatively smooth surface like that of the original tooth enamel before the acid etch. Thereafter, the heavy metal covering said surface is converted into the corresponding heavy metal sulphide which is resistant to decay and to caries producing acids.

27 Claims, No Drawings

METHOD OF REMINERALIZING AND IMMUNIZING TOOTH ENAMEL FOR THE PREVENTION AND CONTROL OF TOOTH DECAY AND DENTAL CARIES

This application is a continuation-in-part of application Ser. No. 471,003, filed May 17, 1974 now abandoned.

BACKGROUND OF THE INVENTION

Dental decay and caries usually occurs as the result of attack by acids in the mouth and saliva. The hydrogen ions of such acids leach out and replace the calcium ions from the surface of the enamel. A lesion or cavity in the enamel thus occurs and if deep enough, renders the tooth vulnerable to attack by decay producing bacteria.

In an effort to protect the enamel surface from attack by such acids, soluble fluoride ions have been topically applied directly onto the surface of the enamel. The consumption of soluble fluoride compounds in water has been shown to be effective in preventing dental decay and caries, but when applied topically to tooth enamel, fluoride ions do not contribute to any significant reduction in dental decay or caries because the fluoride is readily washed off the tooth enamel.

SUMMARY OF THE INVENTION

The inventor has discovered a new method for topically treating tooth enamel to prevent dental decay and caries by replacing the calcium therein with an agent that is absorbed into the enamel and remineralized therewith to form an outer enamel layer which will resist dental decay and caries producing acids, and which will not be readily worn off or washed away as in the case of topically applied fluoride coatings. This new method generally comprises the steps of treating the surface of tooth enamel with a dental etching acid to leach out the positively charged calcium ions thereof, and provide a porous, sponge-like appearing, roughened surface which is negatively charged. This surface is thereafter treated with a solution comprised of the positively charged ions of one or more of the heavy metals which are ionically attracted to the negatively charged surface and are deposited into the sponge-like appearing surface to fill the pores thereof. The calcium lost by the acid etch as aforesaid, is thereby replaced by a heavy metal which remineralizes into a relatively smooth surface. Thereafter, the heavy metal in the surface of tooth enamel is converted into its corresponding heavy metal sulphide which is resistant to caries producing acids and to dental decay. Examples of heavy metals which may be used in the instant invention but without limitation thereto, are zinc, chromium, iron, nickel, tin, lead, cobalt, cadmium, copper, platinum, gold and silver.

EMBODIMENTS OF THE INVENTION

Tooth enamel is negatively charged and will naturally attract positively charged ions such as those of hydrogen and calcium and resist negatively charged ions, such as those of fluorine. Tooth enamel also allows positively charged ions, such as calcium ions, to leave and enter the enamel surface depending upon the relative pH of the surrounding saliva. Saliva generally has a pH between about 7.2 to about 7.4, but when lowered, and the concentration of hydrogen ions becomes relatively high, the hydrogen ions will replace the calcium in the enamel, thereby forming hydrogen phosphate, more commonly referred to as phosphoric acid, which attacks the enamel and leaves a porous, sponge-like appearing roughened surface.

If the pH of the saliva returns to its slightly basic condition, calcium ions naturally occurring in the saliva will replace the hydrogen ions present in the enamel and the previously acid etched surface will be remineralized. This accounts for the "smoothing over" of previously etched enamel surfaces which is observed to occur over a period of time where the saliva is allowed to return to its near neutral pH condition. If the saliva remains acidic, this remineralization may not occur or may not occur at the same rate as will the attack by the acid, and the hydrogen ions will continue to be attracted to and etch the enamel surface.

Thus, by treating the acid-etched surface of the tooth enamel with a heavy concentration of the heavy metals before the natural remineralization with calcium ions occurs, the enamel will be remineralized with the heavy metal ions. The acid etched enamel is sponge-like appearing and porous and the heavy metal ions will penetrate into the labyrinth formed thereby and form an ionic and mechanical interlock therewith.

Hydrogen sulphide gas, which is produced in the mouth by the decomposition of organic matter therein, reacts with the heavy metal remineralized in the surface of the tooth enamel to form the corresponding heavy metal sulphide which is resistant to attack by acids.

When using heavy metals below hydrogen in the electromotive force series of the elements, such as copper, platinum, gold and silver, for example, the ions thereof may not readily or quickly be deposited upon the etched enamel but by use of a reducing agent such as eugenol, hydroquinone, or formeldehyde, for example, such heavy metals will immediately be deposited on the enamel and fill the porous enamel as aforesaid.

In practicing the method of the instant invention zinc ions are preferred because the sulphide of zinc has a color that is white like natural tooth enamel and is therefore esthetically desirable. The sulphides of all the other heavy metals, to the knowledge of the inventor, have a color other than white, and to that extent, they are not preferred for use in the instant invention except on those areas of tooth enamel hidden from view where it would not be aesthetically objectionable.

EXAMPLE I

Teeth immunized with one of the heavy metals are first separated by conventional separation means to expose the contact points therebetween. The enamel of the teeth are then cleaned with flour of pumice, or extra fine silix powder. No oils or coloring matter should be present in the cleaning agents as they may interfere with the immunization. A rubber dam or cotton rolls are applied to the area about the teeth to keep them dry. The enamel to be immunized is treated topically with an aqueous solution comprised of about a 50 to about 85 percent by weight of phosphoric acid for about two minutes and then washed and dried. A white chalky surface will characterize the area that has been acid etched. If no such chalky area appears, the acid etch step should be repeated until the white chalky surface is apparent. The etched area is then treated with an aqueous solution comprising about 40 percent by weight of zinc chloride for about one to two minutes or until a precipitate is observed to appear over the etched surface. This precipitate was viewed under an electron scanning microscope and revealed a remineralization of the enamel. The zinc present in and on the etched surface is thereafter converted to zinc sulphide by the reaction with hydrogen sulphide. Zinc sulphide is white in color and has the same appearance as the white enamel of untreated teeth.

EXAMPLE II

The production of Example I was repeated except that the etched tooth was treated with an ammoniacal solution comprising about 30 percent by weight of silver nitrate. Eugenol is added onto the silver nitrate solution to precipitate the silver therefrom. The silver coating appearing on the etched area thereafter is converted to silver sulphide.

Phosphoric acid and citric acid are two commonly used dental etching acids, but any other acid that will perform the necessary etch may be used as well. Other acids that may be used are the inorganic acids such as hydrochloric, sulphuric, nitric, and the organic acids such as acetic, formic, propionic, trichloroacetic, glutaric, oxalic, malonic, and maleic. The amount of the acid in the dental etching acid may vary considerably, but should be at least about 20 percent by weight when using phosphoric or citric acid. If inorganic mineral acids are used, the amount may be less. The amount of acid however, is not critical to the working of the instant invention except to the extent that sufficient acid must be present to provide the necessary etch without having any substantial excess acid remaining after the etch is finished to eliminate any possible hazard to the surrounding teeth or to the oral cavity.

In using acids that are commercially available for the purpose of etching tooth enamel, a sufficient etch, which removes about 5 to 15 microns of enamel, is achieved if the acid is left on the tooth for approximately 1 to 3 minutes. In actual practice, however, the dental etching acid may evaporate or run off the area to be etched or be so weak that the etch will not be complete. It should be noted that dental etching acid may be intentionally made weak to prevent any excessive etching or damage to the other teeth or to the gums or soft tissue of the mouth if the acid runs off the tooth or when the acid is washed off after the etch. Consequently, the acid and its strength should be selected so that it is just strong enough to accomplish its intended purpose before being rendered ineffectual by neutralization with the calcium in the teeth. In actual practice, however, the acid is sometimes made very weak as a safety precaution for the surrounding teeth, gums, and soft tissue, and thus may require a number of applications to achieve the necessary etch.

The ions of the heavy metals may be provided by dissolving the salt thereof in an appropriate solute such as water, or ammonia, for example. The concentration of heavy metal ions in the solute is not critical to the working of the instant invention except to the extent that a sufficient concentration of heavy metal ions should be present to penetrate into the porous surface without the need for repeated applications.

Solutions of the heavy metals are well suited for use in practicing the method of the instant invention because such solutions are antiseptic, toxic, astringent and escharotic and thereby provide an environment which is detrimental to decay causing bacteria. Non-heavy metals are generally not suited for use in the instant invention to the extent they might be reactive with the tooth enamel, will not form sulphides that are acid resistant and durable, and cannot be deposited into the porous surface of the etched enamel.

Precipitating agents such as aqueous solutions of potassium ferrocyanide or potassium ferriccyanide may be applied to the etched area treated with the heavy metal ions to increase the rate the heavy metal ions precipitate onto and remineralize with said porous enamel surface.

Another beneficial aspect of the instant invention is the abillity of soluble heavy metal compounds to precipitate out mucoprotiens, commonly referred to as "plaque", which adheres to tooth enamel. Plaque is a causitive agent in producing dental decay, such as periodontitis, for example. When tooth enamel is treated with soluble heavy metal compounds during the practice of the instant invention, the plaque thereon will be eliminated and tooth decay will thereby be further reduced.

While the embodiment of the invention shown herein for purposes of disclosure is at present considered to be preferred, it is to be understood that this invention is intended to cover all changes and modifications to the disclosed embodiment which fall within the scope and spirit of the invention.

What I claim as my invention is:

1. A method for remineralizing and immunizing tooth enamel to prevent and control tooth decay and dental caries, comprising the steps of:
   a. etching tooth enamel with a dental etching acid to leach out the positively charged calcium ions thereof and to provide a porous, sponge-like appearing and roughened surface which is negatively charged,
   b. treating said surface with a solution comprised of the positively charged ions of a heavy metal or a compatible mixture of heavy metal ions which are ionically attracted to said negatively charged surface and are deposited in and onto said porous surface which is remineralized with said heavy metal ions to form a relatively smooth surface on said tooth enamel, and
   c. allowing the heavy metals in the surface of the tooth enamel to react with sulphur bearing compounds to form the corresponding heavy metal sulphide thereof which is resistant to caries producing acids and to dental decay.

2. The method of claim 1 wherein said heavy metal is zinc.

3. The method of claim 1 wherein said heavy metal is chromium.

4. The method of claim 1 wherein said heavy metal is iron.

5. The method of claim 1 wherein said heavy metal is nickel.

6. The method of claim 1 wherein said heavy metal is tin.

7. The method of claim 1 wherein said heavy metal is lead.

8. The method of claim 1 wherein said heavy metal is cobalt.

9. The method of claim 1 wherein said heavy metal is cadmium.

10. The method of claim 1 wherein said heavy metal is copper.

11. The method of claim 1 wherein said heavy metal is platinum.

12. The method of claim 1 wherein said heavy metal is gold.

13. The method of claim 1 wherein said heavy metal is silver.

14. A method for remineralizing and immunizing tooth enamel to prevent and control tooth decay and dental caries, comprising the steps of:
   a. etching tooth enamel with a dental etching acid to leach out the positively charged calcium ions thereof and to provide a porous, sponge-like appearing roughened surface which is negatively charged,
   b. treating said surface with a solution comprised of the positively charged ions of a heavy metal or a compatible mixture of heavy metal ions which are below hydrogen in the electromotive force series for metals, said heavy metal being ionically attracted to said negatively charged surface,
   c. applying a reducing agent to said heavy metal solution to deposit said heavy metal in and onto said porous surface which is remineralized with said heavy metal to form a relatively smooth surface on said tooth enamel, and
   d. allowing the heavy metals in the surface of the tooth enamel to react with sulphur bearing compounds to form the corresponding heavy metal sulphide thereof which is resistant to caries producing acids and to dental decay.

15. The method of claim 14 wherein said heavy metal is copper.

16. The method of claim 14 wherein said heavy metal is platinum.

17. The method of claim 14 wherein said heavy metal is gold.

18. The method of claim 14 wherein said heavy metal is silver.

19. The method of claim 14 wherein said heavy metal is silver and said reducing agent is eugenol.

20. The method of claim 14 wherein said heavy metal is silver and said reducing agent is formaldehyde.

21. The method of claim 14 wherein said heavy metal is silver and said reducing agent is hydroquinone.

22. A method for remineralizing and immunizing tooth enamel to prevent and control tooth decay and dental caries, comprising the steps of:
   a. etching tooth enamel with a dental etching acid to provide a porous, sponge-like appearing and roughened surface of at least about 5 microns in depth,
   b. treating said surface with a solution comprised of a soluble heavy metal compound or a compatible mixture of heavy metal compounds to deposit said soluble heavy metal into and onto said porous etched surface to form a relatively smooth surface thereon, and
   c. allowing said heavy metal to react with sulphur bearing compounds to form the corresponding heavy metal sulphide thereof which is resistant to caries producing acids and to dental decay.

23. The method of claim 22 wherein said heavy metal is zinc.

24. The method of claim 22 wherein said heavy metal is silver and a reducing agent is added thereto to deposit the silver into and onto said etched, porous surface.

25. The method of claim 24 wherein said reducing agent is eugenol

26. The method of claim 24 wherein said reducing agent is formaldehyde.

27. The method of claim 24 wherein said reducing agent is hydroquinone.

* * * * *